United States Patent
Davis et al.

[11] Patent Number: 6,148,223
[45] Date of Patent: Nov. 14, 2000

[54] TRANSILLUMINATOR DEVICE

[76] Inventors: James M. Davis, 4687 Pond Apple Dr. S., Naples, Fla. 33999; Martin J. Blum, 9570 Crescent Garden Dr., Naples, Fla. 34109

[21] Appl. No.: 09/054,796

[22] Filed: Apr. 3, 1998

Related U.S. Application Data

[60] Provisional application No. 60/042,506, Apr. 4, 1997, and provisional application No. 60/061,774, Oct. 10, 1997.

[51] Int. Cl.[7] .................................................. A61B 5/00
[52] U.S. Cl. ........................... 600/407; 600/476; 359/894
[58] Field of Search ..................................... 600/473–478, 600/479, 310, 344, 407; 359/894

[56] References Cited

U.S. PATENT DOCUMENTS 5,812,314  9/1998  Kuriaki et al. ........................... 359/894
5,851,181  12/1998  Talmor ..................................... 600/407

*Primary Examiner*—Ruth S. Smith
*Attorney, Agent, or Firm*—William E. Noonan

[57] ABSTRACT

A medical transilluminator device is disclosed. The device includes a fiberoptic cable that is interconnected at one end to a fiberoptic illuminator. The opposite end of the cable is interengaged to a transilluminating spacer component that transmits light toward tissue being examined. A light intensity adjusting mechanism may be interengaged between the fiberoptic cable and the spacer component.

17 Claims, 3 Drawing Sheets

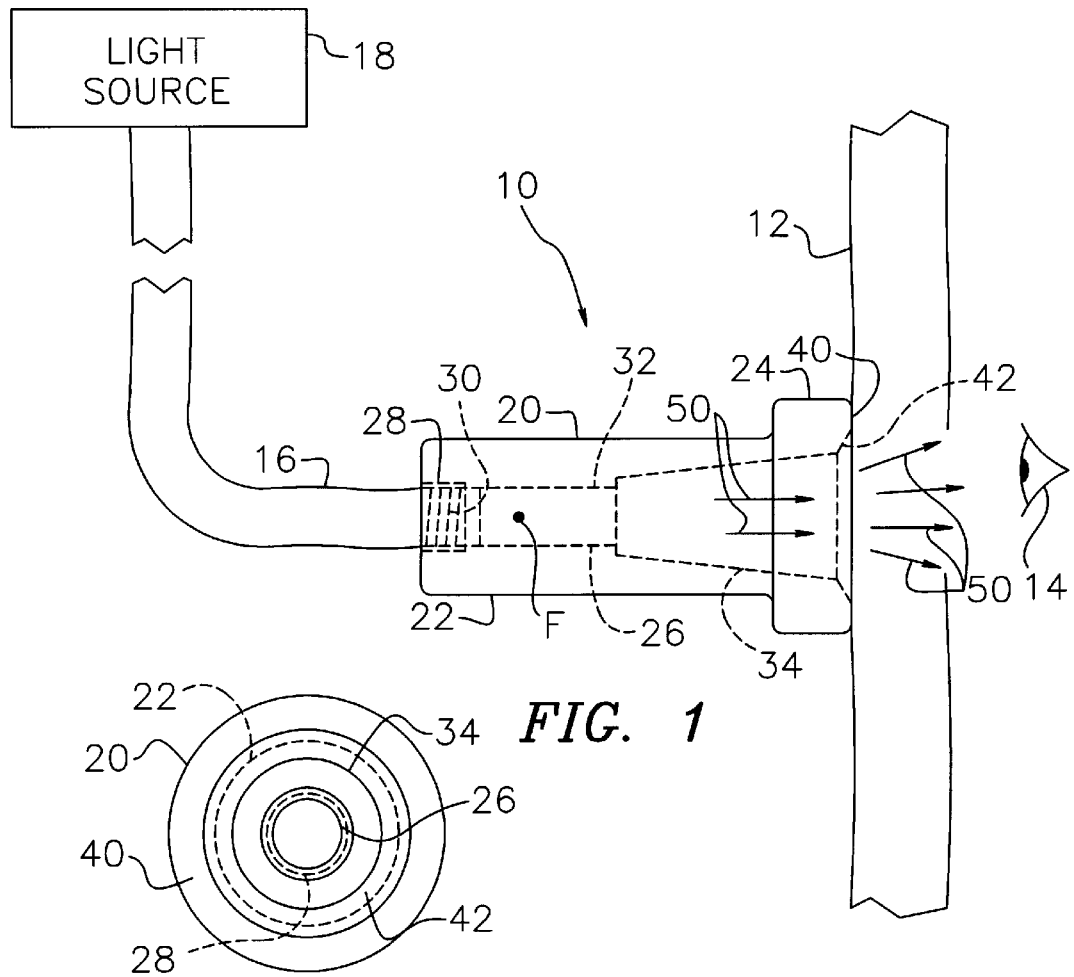
*FIG. 1*
*FIG. 2*
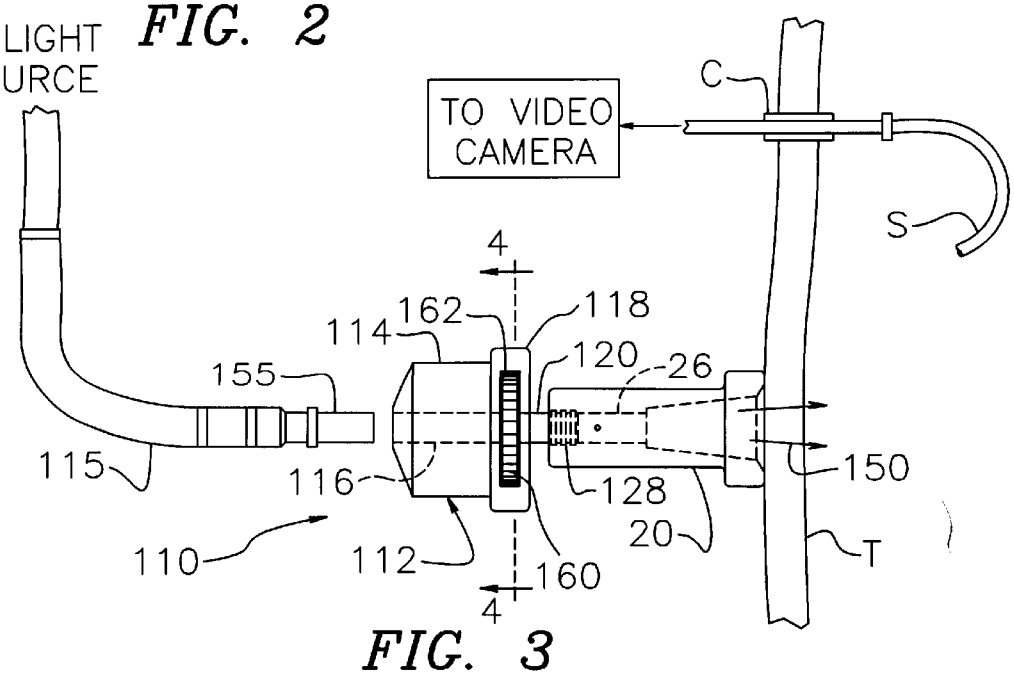
*FIG. 3*

TRANSILLUMINATOR DEVICE

RELATED APPLICATION

This application claims the benefit of the priority dates of United States Provisional Patent Application Serial No. 60/042,506 filed Apr. 4, 1997 and Ser. No. 60/061,774, filed Oct. 10, 1997.

FIELD OF THE INVENTION

This invention relates to a transilluminator device and, more particularly, to a device for fiberoptically illuminating human tissues and blood vessels so that the proper location for surgical incisions may be determined.

BACKGROUND OF THE INVENTION

Various medical procedures require transillumination of the skin or other human tissue. For example, premature babies often require intravenous (IV) feeding. In order to determine the most appropriate location to insert the IV device, the child's skin is transilluminated, typically by a conventional fiberoptic cable. Similarly, for older individuals, certain surgical operations and other medical procedures require the physician to initially determine the location of the patient's veins and other blood vessels in order to avoid these areas when cutting through the skin or other tissue. Usually, the tissue in question is examined by first introducing a scope into the body through a cannula inserted through the tissue. The scope is directed toward the tissue. The physician transilluminates the tissue using a standard fiberoptic cable. This enables blood vessels to be detected by the scope.

Conventional fiberoptic cables exhibit a serious drawback when used in the above-described manner. In order to properly transilluminate the skin or other tissue, the light projecting end of the cable typically must be placed directly against or in close proximity with the outer surface of the skin. As a result, the light is focused onto the skin with an intensity that is apt to burn the patient. Premature infants and other small children have particularly sensitive skin which is highly susceptible to such burns.

Standard transillumination techniques exhibit several other shortcomings. For example, none of the known devices enables the physician or other person manipulating the distal end of the fiberoptic cable to adjust the intensity of light used for transillumination. Such light adjustments must be performed by an assistant at the illuminator. This results in delays, possible miscommunications and intensity misadjustments. Likewise, there is no transilluminator presently available which enables the physician or other personnel manipulating the instrument to quickly and reliably switch the light on and off through the cable. This procedure again must be performed at the illuminator.

SUMMARY OF INVENTION

It is therefore an object of the present invention to provide a medical transilluminator device that effectively illuminates a patient's skin or other tissue so that the location of veins and other blood vessels is quickly and accurately ascertained.

It is a further an object of this invention to provide a transilluminator device that effectively illuminates a patient's skin or other tissue without burning the patient.

It is a further object of this invention to provide a transilluminator device that is particularly safe for use with premature infants and small children.

It is a further object of this invention to provide a transilluminator device that is quick, easy and convenient for virtually all medical personnel to operate and which does not require special training or undue care to use.

It is a further an object of this invention to provide a transilluminator device that may be used with virtually all conventional sources of fiberoptic lighting.

It is a further object of this invention to provide a transilluminator device which enables the transmitted light to be switched on and off in a quick, convenient and reliable manner by the physician or other medical personnel manipulating the transilluminator.

It is a further object of this invention to provide a transilluminator, which enables light intensity to be adjusted in a quick, convenient, and reliable manner by the physician or other medical personnel manipulating the transilluminator.

It is a further object of this invention to provide a transilluminator, which concentrates light effectively onto the location being examined and which significantly reduces ambient light dispersion.

This invention features a transilluminator device, including a fiberoptic cable or other light conductor having a first end that is operably interengaged with a light source. An opposite, second end of the fiberoptic cable is communicably interengaged with a transilluminating spacer component. The spacer component includes means for transmitting light from the fiberoptic cable to an outlet of the transilluminating spacer. The outlet of the transilluminating spacer is engaged with human tissue such that the tissue is transilluminated. The spacer thermally insulates that tissue from the cable.

In a preferred embodiment, the transillumination device also includes means for controlling the intensity of light transmitted through the device. Such means for controlling may interengage the second end portion of the fiberoptic cable and the transilluminating spacer component. The means for controlling may include a housing having an optical passageway formed therethrough. An intensity adjustment wheel may be rotatably mounted within the housing. The intensity adjustment wheel may include a graduated series of openings. The wheel is rotated to place a selected opening in the passageway formed through the housing. That opening allows a predetermined intensity of light to be transmitted from the fiberoptic cable to the transilluminating spacer component.

Alternatively, the means for controlling intensity may include a housing having an interior passageway and a rotatable wheel mounted in the housing, which wheel includes a single opening having a continuously varying width. The wheel is positioned to place a selected portion of the opening in the passageway so that a corresponding, predetermined intensity of light is transmitted by the controlling mechanism. In the version that employs a graduated series of openings, at least one of the openings may include an infrared filter.

The transilluminating spacer component may comprise a metallic or synthetic element having a central channel formed therethrough. Alternatively, the spacer component may include a translucent material. The spacer component may be attached to an output of the intensity controlling mechanism by various light communicating interengagement means.

The transilluminator device may also include means for selectively transmitting light through the device. Such means may include a light transmission wheel that is rotatably mounted within the housing of the transilluminator. A plurality of openings may be disposed radially about the light transmission wheel. The wheel is turned to selectively position either an opening or a solid portion of the wheel in the optical passageway. When an opening is positioned in the passageway, light is transmitted through the transilluminator. When a solid portion of the wheel is positioned in the passageway, no light is transmitted.

An opaque casing or cover may be formed about a portion of the transilluminating spacer. The casing or cover exposes the outlet of the spacer such that light is transmitted through the outlet and onto the tissue or other object being illuminated.

DETAILED DESCRIPTION OF PREFERRED EMBODIMENTS

Other objects, features and advantages will occur from the following description of preferred embodiments and the accompanying drawings, in which:

FIG. 1 is an elevational, partly schematic view of one version of the transilluminator device of this invention;

FIG. 2 is an elevational end view of the transilluminating spacer component;

FIG. 3 is an elevational view of a version of the transilluminating device that includes an intensity control mechanism;

Figure 4:
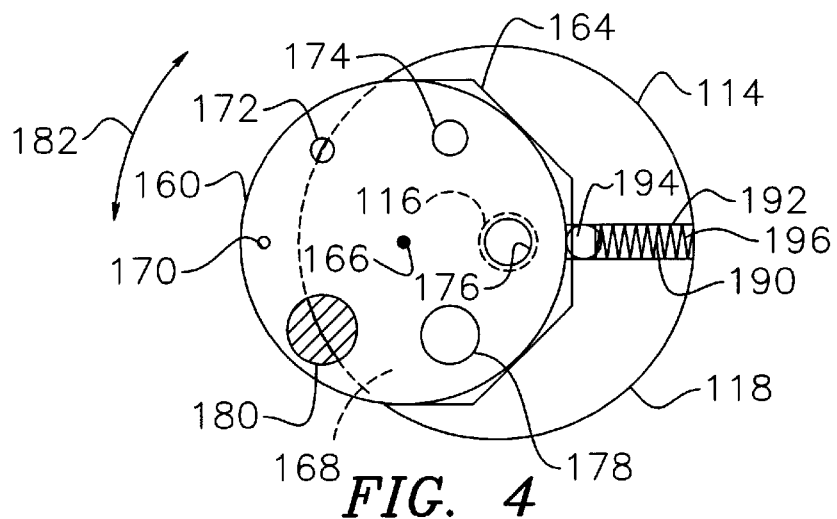
FIG. 4 is a cross sectional view of a preferred intensity control mechanism, which utilizes an intensity adjustment wheel having a graduated series of openings.

There is shown in FIG. 1 a transilluminator device 10, which is designed and intended for transilluminating a section of organic human tissue 12 (e.g. the skin) such that veins and other blood vessels are illuminated when tissue 12 is viewed from the position of the eye of an observer 14. For example, tissue 12 may comprise the hand of a premature infant. The transilluminating device 10 is engaged against the infant's hand to illuminate blood vessels in the hand so that a physician can determine the proper location to insert an IV device.

Transilluminating device 10 includes a standard fiberoptic cable 16 that is secured at a first end to a conventional fiberoptic light source 18. The light source may comprise a halogen, xenon or other type of fiberoptic illuminator. This is typically a conventional device, the details of which are not a part of this invention. In alternative versions, other types of light conductors and light sources may be featured.

The opposite, second end of cable 16 is attached to a transilluminating spacer cup 20. This cup 20 has a generally cylindrical, cross sectional shape, which is best shown in FIG. 2. Cup 20 may be manufactured from stainless steel or a similar metal or metal alloy that is suitable for medical and surgical uses. Alternatively, a disposable plastic material may be used. The cup features a one piece body, including an elongate, cylindrical body portion 22 attached at one end to cable 16, and a large diameter flange 24 unitarily interconnected to body portion 22 and formed at the distal end thereof. A central channel 26 extends fully through cup 20. A light inlet, comprising a threaded receptacle 28 is formed in the cup at one end of central channel 26. This receptacle receives a complementary threaded fitting 30 carried proximate the second end of fiberoptic cable 16. Light is discharged from fitting 30 in a known manner. As a result, the fiberoptic cable is communicably interconnected to cup 20. In alternative embodiments, the second end of cable 16 may be releasably interconnected to cup 20 by various other forms of interconnection that should be well understood to those skilled in the art of fiberoptic cables. For example, an unthreaded end fitting and inlet may be slidably or otherwise snugly interengaged. The precise forms of the cable end fitting and complementary inlet are not a limitation of this invention.

Central channel 26 includes a relatively small diameter portion 32 and a relatively large, expanding diameter portion 34. As best illustrated in FIG. 1, channel portion 34 expands in diameter from its rearward end adjacent channel portion 32, toward its opposite, forward end such that portion 34 exhibits a generally truncated conical shape. The diameter at the forward end (i.e. the end engaging the skin 12) is approximately $\frac{1}{10}$ inch greater than the diameter proximate the rearward end. The forward end of the central channel defines an outlet from which light is discharged. Flange 24 includes an annular surface 40 that surrounds the outlet and engages the skin or other tissue. The flange also includes an inner, generally annular chamfered surface 42 that interconnects annular surface 40 and the leading edge of channel portion 34. In a preferred embodiment, flange 24 of cup 20 includes an outer diameter of approximately 0.75 inches. The cup has a length of approximately 1.34 inches. These dimensions may be varied within the scope of this invention.

In operation, cup 20 is attached threadably or otherwise to cable 16 and the opposite end of the cable is operably interengaged with light source 18. As a result, light is directed through cable 16 and into channel 26 of cup 20. This light is focused at point F within channel 26, which is typically 60–80 thousandths of an inch from the end of cable 16. The light is then transmitted through the remainder of channel 26 and, in particular, from portion 32 into expanding portion 34. This light diametrically expands and is discharged or projected, as indicated by arrows 50, from the forward end of the cup through tissue 12. As a result, with the leading annular surface 40 directly engaging the skin, the surgeon or other observer 14 is able to clearly and conveniently observe the illuminated blood vessels in the tissue. This area of the tissue can then be avoided when an intravenous or other type of incision is made. Because the inlet and outlet are spaced apart and the focal point F is spaced over an inch away from the surface of tissue 12, undue heating and burning of the tissue are averted. The tissue is in essence thermally insulated from the fiberoptic cable. The risk of burning is further reduced because cup 20 acts as a heat sink to dissipate heat from the light emitted from the cable.

As illustrated in FIG. 3, an alternative version of this invention comprises a transilluminator 110. In this embodiment, an intensity adjusting mechanism 112 is interengaged between a fiberoptic cable 115 and spacer cup 20. It should be understood that cup 20 is identical in construction and operation to the cup shown in FIG. 1.

Intensity adjusting mechanism 112 includes a housing 114 having a central passageway 116 formed therethrough. A flange 118 is formed at a forward end of housing 114. A unitary threaded fitting 120 projects forwardly from flange 118 and is communicably interengaged with a complementary threaded inlet 128 formed in cup 20. It should be understood that central passageway 116 extends completely through mechanism 112 and exits through fitting 120. It should also be understood that various other types of fittings may be used to communicably interconnect mechanism 112 and cup 20.

An intensity adjustment wheel 160 is rotatably mounted within housing 114 such that the peripheral edge of the wheel protrudes through a slot 162 in flange portion 118. This is shown more clearly in FIG. 4. As illustrated therein, wheel 160 is offset relative to flange 118 and is received within a recess 164 formed in the flange. Wheel 160 is rotatably mounted by an axial pin 166 to a rearward wall 168 of flange portion 118. An analogous wall covers the forward surface of wheel 160 (i.e. the surface facing outwardly from the page in FIG. 4).

Intensity adjustment wheel 160 includes a graduated series of progressively larger diameter circular openings 170, 172, 174, 176, 178 and 180 that are formed at regularly spaced intervals about the wheel. By rotating the wheel as indicated by double headed arrow 182, openings 170–180 may be selectively positioned across passageway 116. As a result, a predetermined intensity of light (determined by the diameter of the selected opening) is transmitted through the passageway. If only a minimal amount of light is desired, the wheel is rotated so that smaller diameter opening 170 is positioned across passageway 116. Conversely, if a maximum amount of light is desired, large opening 180 is positioned across the passageway. Additionally, an optional infrared filter is fitted on opening 180. The remaining openings may be fully exposed or include transparent lenses. In alternative embodiments, other varieties of filters may be placed in one or more of the openings.

Each opening in wheel 160 is held in place across passageway 116 by a releasable locking mechanism 190. In particular, flange portion 118 includes a radial slot 192 that houses a bearing 194. The bearing is urged inwardly toward the center of flange portion 118 and into recess 164 by a spring mechanism 196. A plurality of indents or recesses, not shown, are formed about the periphery of wheel 160. Each such indent is positioned on the periphery of wheel 160 adjacent to a respective one of the openings 170–180. When a particular opening, e.g. opening 176, is positioned across passageway 116, spring mechanism 196 urges bearing 194 to engage the corresponding adjacent indent formed in the periphery of wheel 160. This constrains the wheel so that the opening is held in position across passageway 116. Unintended movement of the selected filter is prevented. To adjust the intensity, the operator simply places his or her thumb against the peripheral portion of the wheel that protrudes from housing 114. The wheel is then rotated as indicated by double headed arrow 182. Bearing 194 disengages the notch in which is has previously resided and compresses spring mechanism 196. As a result, the wheel is released and free to rotate. The operator turns the wheel until a new selected opening is placed in position across the passageway. The spring and bearing mechanism re-engage with the notch corresponding to the opening. As a result, the wheel is again held in place until subsequent adjustment is desired.

Figure 5:
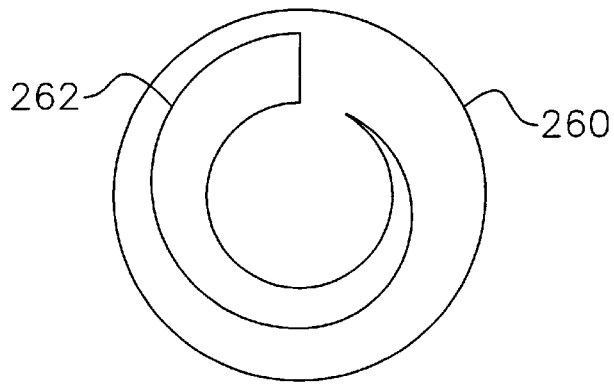
FIG. 5 is an elevational front view of an alternative intensity adjustment wheel employing a single opening that has a continuously varying width.

An alternative intensity adjustment wheel 260 is depicted in FIG. 5. That wheel is mounted in a housing in a manner analogous to wheel 160 shown in FIGS. 3 and 4. Wheel 260 is provided with a single, generally crescent-shaped opening 262. Opening 262 features a continuously expanding width. By rotating wheel 260 in the manner previously described for wheel 160, a selected portion of opening 262 is positioned across the passageway formed through the intensity adjustment mechanism. As a result, a desired intensity of light is transmitted from the fiberoptic cable to the transilluminating spacer component.

As illustrated in FIG. 3, fiberoptic cable 115 includes a standard light projecting end fitting 155. The opposite end of the cable is operably interengaged in a known fashion with a conventional fiberoptic light source. Fitting 155 is introduced into passageway 116 of intensity adjusting mechanism 112. As a result, light is delivered through cable 115 from the light source to the intensity adjusting mechanism. The operator rotates intensity adjusting wheel 160 in the manner described above so that a selected intensity of light is transmitted through mechanism 112 and into channel 26 of spacer cup 20. This light is then directed in the manner indicated by arrows 150 through tissue T.

In either of the above described versions employing an intensity adjustment wheel, significant benefits are achieved. The physician or other medical personnel manipulating the transilluminator is able to adjust the intensity quickly, conveniently and reliably without having to make such adjustments at the illuminator. Instead, intensity can be selected by the operator at the distal end of the cable. The operator accomplishes this using the same hand that is used to hold the transilluminator. The operator simply places his or her thumb on the adjustment wheel and rotates that wheel until a selected opening is positioned in the passageway and a corresponding intensity level is achieved. Directions do not have to be given to assisting personnel, time is saved, and reliability is improved considerably.

In the embodiment of FIG. 3, a videoscope S is accommodated beneath the surface of tissue T by a cannula C. Scopes S detects the light 150 being transmitted through tissue T and determines the precise location of veins or other blood vessels. As a result, these blood vessels may be avoided when a surgical incision is made through tissue T. As in the prior embodiment, the heat from the fiberoptic radiation is dissipated by the spacer so that burning is avoided. Heat is reduced even further by the employment of an infrared filter 180, shown in FIG. 4.

Figure 6:
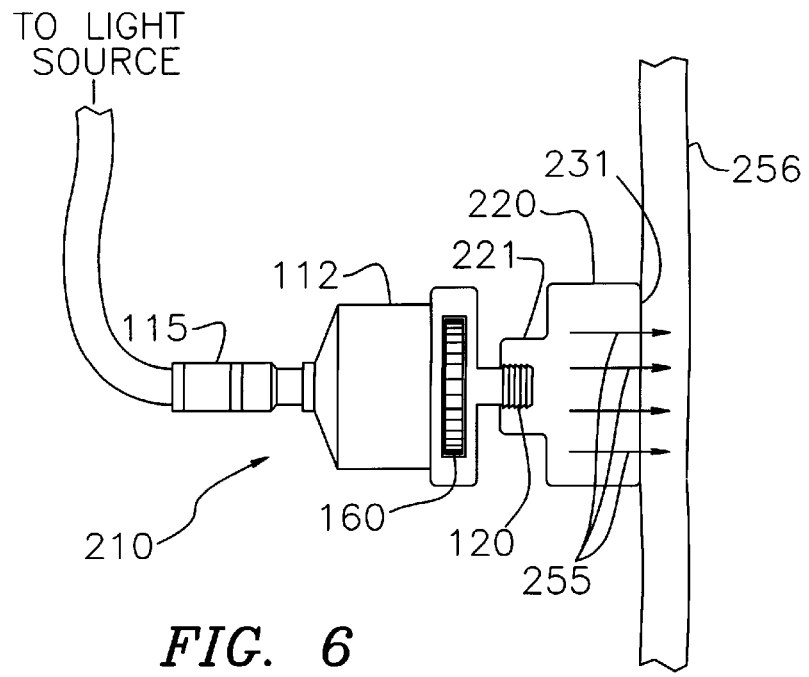
FIG. 6 is an elevational view of an alternative version of the transilluminating device, which employs a translucent spacer component.

FIG. 6 illustrates a transilluminator 210 employing a fiberoptic cable 115 and an intensity adjusting mechanism 112. Each of these components is constructed and operates in the manner previously described. In this embodiment, the previously described spacer cup is replaced by a translucent spacer 220. Spacer 220 is composed of any lightweight translucent component. It should feature a high light transmitting characteristic. A threaded receptacle or analogous inlet fitting 221 extends from a rearward end of spacer 220 and is operably interconnected with a complementary threaded fitting 120 of mechanism 112. In alternative embodiments, various other standard forms of communicable interconnection may be employed between mechanism 112 and spacer 220. In still other versions, a central channel may be formed through the spacer as in the prior embodiment. The front surface of the spacer may have a rounded or contoured shape.

In operation, light is directed from the light source through cable 115 to mechanism 112. As previously described, light adjusting wheel 160 is operated so that a selected intensity of light is transmitted through mechanism 112 to spacer 220. The forward end 231 of spacer 220 functions as an outlet and is placed directly against the outer surface of tissue 256. This light is then transmitted, as indicated by arrows 255, through translucent spacer 220. As a result, the light is projected from the spacer and through tissue 256. This permits the tissue and any veins or blood vessels contained in the tissue to be examined, either visually or through the aid of a scope in the manners previously described. The spacer is preferably disposable so that it may be changed between uses.

Figure 7:
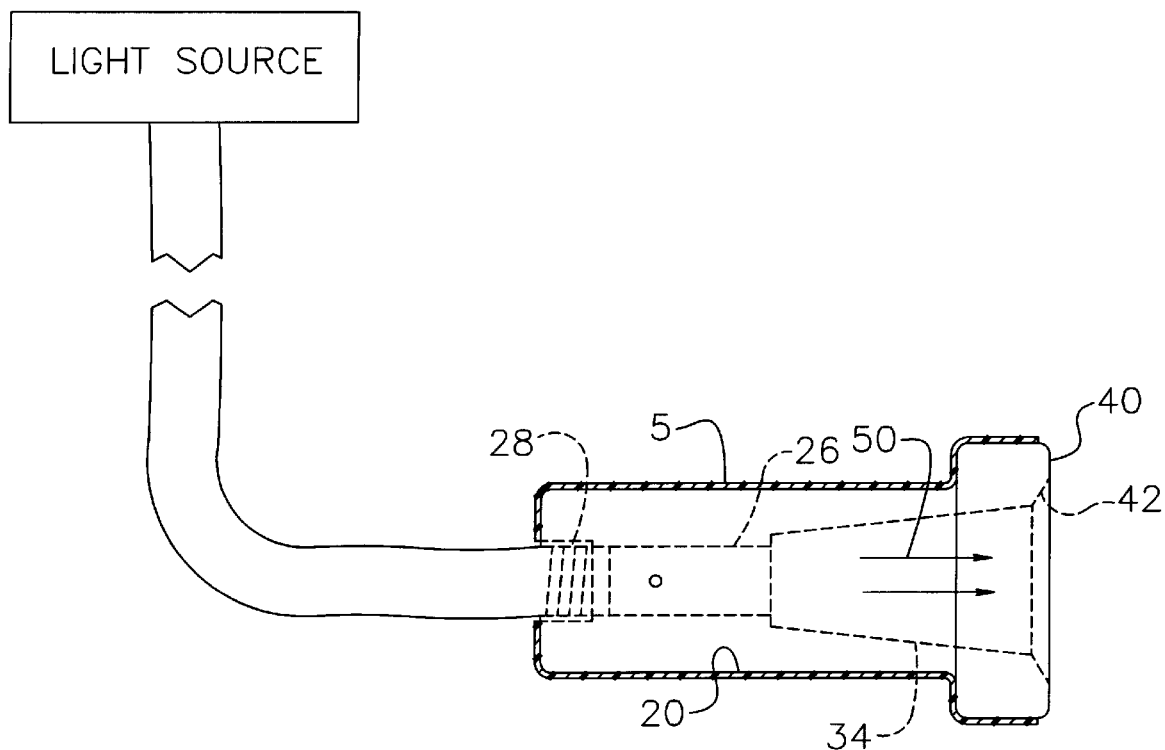
FIG. 7 is a elevational, partly cross sectional and partly schematic view of a transilluminating device wherein the spacer is partially covered by an opaque casing.

FIG. 7 illustrates a transilluminator device 10, as shown in FIG. 1, with the addition of an opaque casing 5 that covers much of the surface of spacer cup 20. Opaque casing 5 typically comprises a light blocking plastic material or other form of opaque coating. The casing covers the entire spacer, with the exception of receptacle 28, the central channel 26, expanding portion 34 and the discharge portion of cup 20, including surfaces 40 and 42. Opaque casing 5 prevents light from dispersing radially or transversely through spacer cup 20. Instead, the light is channeled exclusively in the direction of arrows 50 through the discharge end of spacer cup 20. This prevents potentially distracting ambient light from being dispersed from the spacer cup and provides the examining physician with improved viewing. It should be noted that this version is particularly advantageous when the body of the spacer cup is composed of a translucent material.

Figure 8:
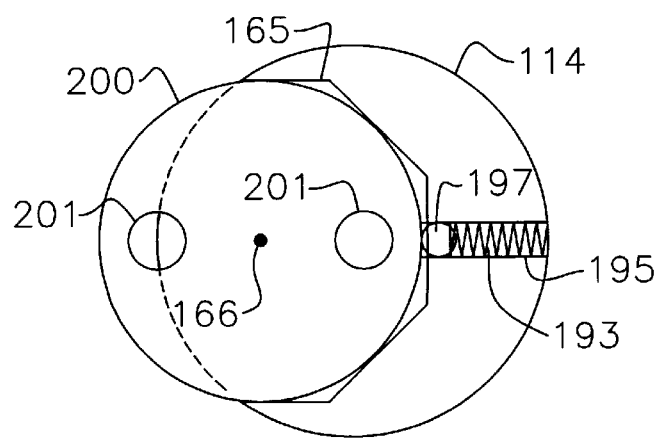
FIG. 8 is a cross sectional view of a light transmitting wheel that is mounted in the transilluminator housing and which is operated as an on/off switch to selectively transmit light through the transilluminator.

Light through the transilluminator may be selectively switched on and off by a light transmitting wheel 200, shown in FIG. 8. This wheel employs a structure that is analogous to the previously described intensity adjustment wheel. Specifically, light transmitting wheel 200 is mounted rotatably within housing 114, such as by axial pin 166. This pin may be the same pin that axially mounts the intensity adjustment wheel. Wheel 200 is disposed in a recess 165 of housing 114. A spring 193 located in a slot 195 urges a bearing 197 into engagement with the peripheral edge of wheel 166. The wheel includes a plurality of circular openings 201 that are spaced radially about wheel 200. In the embodiment disclosed in FIG. 8, a pair of openings 201 are positioned 180 degrees apart on the wheel. The remainder of the wheel is solid.

To transmit light through the previously described passageway in housing 114, wheel 200 is rotated to position a selected one of the openings 201 in front of the passageway. One of the openings is shown in such a position in FIG. 8. Light passing through the transilluminator passageway is subsequently switched off by simply rotating wheel 200 in either direction until a solid portion of the wheel is disposed in front of the passageway. This blocks light from passing through the passageway and the transilluminator. The peripheral edge of wheel 200 typically includes four position-defining indents that are interengagable with bearing 197. Two of the indents are formed adjacent respective openings 201. The other indents are formed at radial positions that are between the openings 201 and approximately 180 degrees apart. The wheel is rotated such that spring 193 urges bearing 197 into a respective one of the indents. This holds the wheel in place at a selected position. When one of the openings 201 is disposed in front of the passageway, light is transmitted through the transilluminator. Alternatively, when a solid portion of the wheel is disposed in front of the passageway, no light is transmitted. Accordingly, the transilluminator may be switched on or off by simply rotating the wheel 200 approximately 90 degrees until a succeeding indent interengages bearing 197. This selectively and alternately positions either an opening or a solid portion of wheel 200 in front of the passageway so that light is transmitted or blocked and the apparatus is switched on or off, respectively.

The above described on/off switch facilitates the use of this device considerably. The physician or other medical personnel who is manipulating the transilluminator is able to turn the transmitted light on or off quickly, conveniently, and reliably. Instructions do not have to be given to an assistant. Time is saved and miscommunications are eliminated. This operation is accomplished with a simple and quick movement of the user's thumb in a manner similar to that described for the intensity adjustment wheel.

In alternative embodiments of this invention, the intensity adjusting mechanisms disclosed herein may be replaced by other types of light controlling devices that are communicably interconnected between the fiberoptic cable and the spacer component. For example, an adjustable iris, as disclosed in co-pending U.S. patent application Ser. No. 08/719,838 may be utilized. It should also be understood that various types of fiberoptic cables, including those employing a liquid light transmitting medium may be utilized with this transilluminator.

Accordingly, the present invention permits sections of tissue to be effectively transilluminated and investigated so that the precise location of blood vessels may be quickly and conveniently determined. The transilluminator device of this invention is lightweight and easy to operate. It virtually eliminates any chance that the patient or the patient's tissue will be burned during the transillumination process. As a result, this invention provides significant benefits when used for surgical and other medical procedures.

It will thus be seen that the objects made apparent from the preceding description are sufficiently obtained and certain changes may be made in the above construction without departing from the scope of the invention. It is intended that all matter contained in the above description and shown in the accompanying drawings be interpreted as illustrative and not in an imitative sense. Although specific features of the invention are shown in some drawings and not others, this is for convenience only as each feature may be combined with any or all of the features in accordance with the invention. Other embodiments, within the scope of this invention, will occur to those skilled in the art.

What is claimed is:

1. A device adapted to be used in combination with a light source for transilluminating a sample of organic tissue, said device comprising:

a light conductor having a first end that is operably interengagable with the light source, said conductor capable of emitting light from a distal second end thereof, which light generates heat proximate said distal end of said conductor; and a transilluminating spacer body that is communicably interengaged with said distal end of said conductor, said spacer body including an inlet that is communicably engaged with and capable of receiving the emitted light from said light conductor, an outlet spaced apart from said inlet and an unobstructed and completely open channel that extends fully through said body from said inlet to said outlet for transmitting light from said inlet to said outlet, which light is discharged from said outlet, said conductor including a fiberoptic cable that directs said light to a focal point within said channel between said inlet and said outlet, whereby said outlet is directly engagable with the organic tissue sample to transilluminate the sample; said spacer body providing means for thermally insulating the tissue sample from said distal end of said light conductor.

2. The device of claim 1 further including means interengaged between said light conductor and said spacer body for controlling the intensity of light transmitted through said body.

3. The device of claim 2 in which said means for controlling include a housing having an interior passageway communicably interconnecting said conductor and said inlet and through which light from said conductor is transmitted and further including a wheel rotatably mounted in said housing and having a plurality of differently sized apertures formed therein, said wheel being rotated to position a selected aperture across said interior passageway, whereby a corresponding intensity of light is transmitted from said conductor to said spacer body.

4. The apparatus of claim 3 in which said wheel includes a peripheral edge that protrudes through a slot in said housing, said peripheral edge being engaged to rotate said wheel within said housing.

5. The apparatus of claim 3 in which said apertures comprise of a graduated series of discrete openings.

6. The device of claim 5 in which at least one of said openings includes an infrared filter.

7. The apparatus of claim 3 in which said apertures comprise a single, generally crescent-shaped opening having a continuously expanding width.

8. The device of claim 1 in which said light conductor comprises a fiberoptic cable.

9. The device of claim 8 in which said cable includes a focal point that is disposed between said inlet and said outlet of said spacer body when said spacer body is interengaged with said cable.

10. The device of claim 1 further including means for selectively transmitting and blocking light through said spacer body.

11. The device of claim 10 in which said means for selectively transmitting and blocking light include a housing having an optical passageway formed therethrough, which housing is communicably interconnected between said spacer body and said light conductor, said means for selectively transmitting and blocking further including a light transmission wheel that is rotatably mounted within said housing, said wheel including a plurality of alternating openings and solid portions disposed radially therein, said wheel being rotated to selectively position one of an opening and a solid portion in said optical passageway to respectively transmit and block light through said passageway.

12. The device of claim 1 further including a casing formed about at least a portion of said body and exposing said outlet such that light is transmitted through said outlet and onto the tissue being transilluminated and transverse dispersion of said light from said spacer body, otherwise than through said outlet, is restricted.

13. The device of claim 1 in which said body comprises a heat sink that dissipates heat from the received light between said inlet and said outlet.

14. The device of claim 1 in which said focal point is located no closer than 60 thousandths of an inch and no farther than 80 thousandths of an inch from the second end of said cable.

15. The device of claim 1 in which said focal point is spaced at least one inch away from said outlet.

16. The device of claim 14 in which said focal point is spaced at least one inch away from said outlet.

17. A device for use in combination with a light source to transilluminate a sample of organic tissue, said device comprising:

a light conductor having a first end that is operably interengagable with the light source, said conductor capable of emitting light from a distal second end thereof, which light generates heat proximate said distal end of said conductor; and a transilluminating spacer body that is communicably interengaged with said distal end of said conductor, said spacer body including an inlet that is communicably engaged with and capable of receiving the emitted light from said light conductor, an outlet spaced apart from said inlet, and a single, unobstructed and completely open channel formed axially centrally through said body from said inlet to said outlet, said channel transmitting light from said inlet to said outlet, which light is discharged from said outlet, said conductor directing light emitted therefrom to a focal point within said channel, said focal point being spaced at least 60 millimeters and not greater than 80 millimeters apart from said distal end of said conductor, said focal point being spaced at least 1 inch apart from said outlet of said body, whereby said outlet is directly engagable with the organic tissue sample to transilluminate that sample; said spacer body comprising a heat sink and providing means for thermally insulating the tissue sample from said distal end of said light conductor.

* * * * *